United States Patent [19] [11] 4,322,964
Melgaard et al. [45] Apr. 6, 1982

[54] GAS ANALYZER CALIBRATION APPARATUS

[75] Inventors: Hans L. Melgaard; Gary H. Mercier, both of Minneapolis, Minn.

[73] Assignee: Despatch Industries, Inc., Minneapolis, Minn.

[21] Appl. No.: 112,135

[22] Filed: Jan. 14, 1980

[51] Int. Cl.³ ............................................. G01N 37/00
[52] U.S. Cl. ....................................................... 73/1 G
[58] Field of Search ............................................ 73/1 G

[56] References Cited
U.S. PATENT DOCUMENTS 4,094,187 6/1978 Navarre, Jr. .................. 73/421.5 A Primary Examiner—S. Clement Swisher
Attorney, Agent, or Firm—Steven G. Parmelee; James R. Haller

[57] ABSTRACT

A gas analyzer calibration apparatus. The apparatus operably connects between a monitored gaseous environment and a gas analyzer. The apparatus includes a vacuum pump for drawing test gases from the monitored environment through the apparatus and through the analyzer. A fluidic gate selectively allows or impedes the flow of test gases to the analyzer and provides calibration gases to the analyzer at the analyzer's demand rate, and may be heated to prevent the condensation of hot test gases flowing therethrough. The fluidic gate will pass both span calibration gases and zero calibration gases, as desired. A vacuum breaker provides atmospheric gases for use as a zero calibration gas.

6 Claims, 4 Drawing Figures

GAS ANALYZER CALIBRATION APPARATUS

TECHNICAL FIELD

This invention relates generally to pneumatic pathway control systems, and more particularly to gas analyzer calibration systems.

BACKGROUND ART

Industrial ovens are often used to heat substances that yield gases capable of explosive combustion if sufficiently concentrated. To avoid the dangers of such combustion, these ovens have venting systems to purge the oven chamber during the heating cycle. Industry standards as promulgated by the National Fire Prevention Association identify two methods for safely using such vented ovens.

By the first method, if the operator does not known the concentration level of explosive gases in the oven chamber, he must frequently purge the oven chamber. Although the operator will never be sure of the actual concentration level, he can be reasonably assured that an explosive concentration cannot accumulate.

As an alternative, the operator may analyze the exhaust gases from the oven and determine the actual concentration level of the explosive gases. An analyzer for doing this may be found in U.S. Pat. No. 4,116,612. By relying upon such analysis, the operator need only purge the oven chamber upon reaching a maximum acceptable concentration level. This technique has many benefits over the first method, since frequently purging the oven chamber requires a significantly higher expenditure of energy to continually reheat the newly introduced oven atmosphere.

Gas analyzers generally include a sensor to sense the concentration level of a particular gas or gases. These analyzers are generally calibrated by establishing a zero condition and an upper acceptable limit. To establish this upper acceptable limit, the operator exposes the sensor to a known concentration of calibration gas called span calibration gas. Once calibrated, the analyzer will only take affirmative action when concentrations exceed this upper acceptable limit.

If the analyzer should become uncalibrated and accept a higher concentration of explosive gases without warning or appropriate action, a dangerous condition may arise. Because of this, some prior art devices provide for mechanisms whereby the analyzer may be occasionally recalibrated by reintroducing both zero calibration gases and span calibration gases. In general, these devices have an in-line solenoid valve between the oven chamber and the analyzer such that the flow of test gases to the analyzer may be shut off. Then, other valves will be opened to allow the zero or span calibration gases to be injected into the analyzer. Certain problems, however, have arisen as a result of these designs.

First, such mechanisms do not necessarily insure accurate calibration. In general, the analyzer operates by sucking exhaust gases into its sensor chamber by means of a vacuum pump. By injecting the zero or span calibration gases into the sensor chamber, however, the calibration gases will be introduced at a pressure higher than normal operating pressures. This difference may be significant, since an analyzer calibrated for a certain concentration level of gases delivered at one pressure may not properly respond to that same concentration level delivered at a different pressure. Consequently, the analyzer may accept a dangerously high concentration level even though apparently calibrated.

Second, using a solenoid valve to close off the test gas line to the analyzer has often been unsatisfactory. The test gases from the oven chamber will often include various silicones, resins, plasticizers, fillers and varnishes. These materials may collect in the solenoid valve orifice and cause the valve to become partially plugged. This becomes particularly troublesome when the temperature of the test gases exceeds the temperature rating for the solenoid valve, as will often be the case. Under such conditions, the solenoid value must be maintained at a lower temperature than the test gases, and this promotes condensation of the test gas material within the solenoid valve, thereby worsening the plugged condition. This may again result in a dangerous condition since the analyzer, even if properly calibrated, may not be receiving a sufficient sample quantity to make an accurate reading.

Therefore, a need exists for a combustible gas analyzer calibration apparatus that does not use solenoid valves in the test gas flow line to the analyzer, and for an apparatus wherein calibration gases will be introduced into the analyzer at substantially the same pressure as the test gases.

DISCLOSURE OF THE INVENTION

The instant invention is directed towards a gas analyzer calibration apparatus that includes a fluidic gate for selectively blocking the test gas line without the use of a solenoid valve in the test gas line, and for providing the analyzer with a supply of calibration gas at conditions substantially equivalent to those under which the test gases are delivered. The apparatus further includes a vacuum pump and vacuum breaker system whereby atmospheric gases may be introduced into the apparatus and used as a zero calibration gas, thereby eliminating the need for an independent source of pressurized zero calibration gas.

In general, the oven system will be provided with a pickup tube for receiving test gases and an exhaust tube for returning analyzed gases back into the oven system. A typical gas analyzer system will have an input port for receiving test gases from the analyzer. The gas analyzer calibration apparatus disclosed herein operably connects between these two systems.

Since analyzers generally operate by sucking the gas samples through the system, the apparatus of the invention includes a vacuum pump that has a vacuum input operably connectable to the exhaust port of the analyzer. The vacuum input of the vacuum pump also connects to the output of a vacuum breaker having an input open to atmospheric gases. The vacuum pump also has a compression output that operably connects to the exhaust tube input of the monitored oven system.

The vacuum pump sucks exhaust gases from the oven system through the analyzer, and then compresses these gases and pumps them back into the oven system. The vacuum breaker serves a dual function. First, as may be desired, it reduces the effect of the vacuum pump by allowing atmospheric gas to be sucked into the vacuum pump as well as test gases. The second function of the vacuum breaker is to supply atmospheric gases as a zero calibration gas, as disclosed further below.

Test gases are routed from the pickup tube in the oven system and into the analyzer by way of a fluidic gate. This fluidic gate consists of a steel block, or block of other suitable material, having a first pathway disposed therethrough. One end of the pathway forms a calibration gas input. The fluidic gate also includes a second pathway having one end connecting to the first pathway and the remaining end forming an output for connection to the input port of the analyzer. Importantly, the second pathway and the first pathway connect to form an accute angle between the second pathway and the calibration gas input of the first pathway.

The calibration gas input of the first pathway may have a smaller interior diameter than the remainder of the first pathway, preferably located near the intersection between the first and second pathways.

The calibration gas input of the fluidic gate operably connects through a solenoid valve to a calibration gas input port, where pressurized calibration gas may be introduced into the apparatus. In general use, this solenoid valve will be closed, and test gases will enter the fluidic gate through the test gas input and follow the gentle angle down through the second pathway. The test gases will then travel into the analyzer input port.

To introduce a span calibration gas into the analyzer, the solenoid value will be opened and pressurized calibration gas will enter the calibration gas input of the fluidic gate. This stream will be forced through the venturi and exit at the intersection between the first and second pathways. When properly regulated, the calibration gas pressure will exceed the test gas stream, such that the flow of test gas through the fluidic gate will be blocked and no further test gases will enter the analyzer.

Because of the accute angle between the second pathway and the calibration gas input, this stream of calibration gas will not enter the second pathway under pressure. In fact, locating the mouth of the second pathway just below the opening of the venturi will cause a low pressure area to exist at the mouth, such that the analyzer may receive calibration gases at its own demand rate as determined by the vacuum pump suction.

The fluidic gate therefore accomplishes two primary functions. Without using a solenoid valve in the test gas line, the fluidic gate will effectively block the flow of test gases into the analyzer. At the same time, the fluidic gate will provide a supply of calibration gas for use by the analyzer without injecting those gases into the analyzer at high pressure.

To provide zero calibration gas, the compression output of the vacuum pump also connects through an input-selective solenoid valve to the calibration gas input line. This solenoid valve selects between one of two inputs; i.e., it will route gases from either the span calibration gas input or from the compression output of the vacuum pump. Therefore, when adjusted to allow flow from the compressor output to enter the fluidic gate, atmospheric gas entering the vacuum pump input through the vacuum breaker will be supplied under pressure from the vacuum pump to serve as a zero calibration gas for the analyzer. The flow of pressurized atmospheric gas will again shut off the flow of test gases in the fluidic gate while entering the analyzer.

To improve operating efficiency, a restriction valve may be located in the compressor output line of the vacuum pump, just subsequent to the zero calibration gas line connection. This restriction valve will maintain greater pressure on the vacuum pump side than on the oven system side, thereby promoting the flow of atmospheric gases into the fluidic gate when such is desired.

To further improve operation, a pressure regulator may be located in the calibration gas line. The span calibration gases and zero calibration gas entering the fluidic valve will then generally do so at a preselected pressure as determined by the pressure regulator.

BRIEF DESCRIPTION OF THE DRAWING

Other features of the instant invention may be more easily understood by reference to the following detailed description, and particularly when considered in view of the appended drawings, wherein:

and FIG. 5 is another enlarged cross-sectioned front elevational view of the fluidic gate of the invention.

BEST MODE FOR CARRYING OUT THE INVENTION

Figure 1:
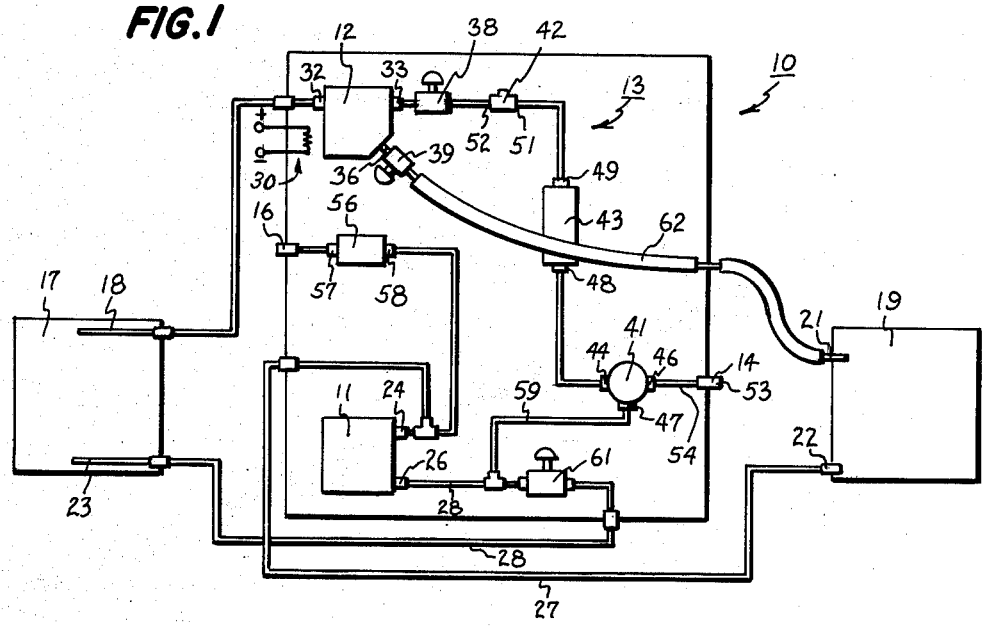
FIG. 1 is a schematic block diagram of the apparatus of the invention as connected between an oven system and a gas analyzer.

Referring to FIG. 1, the apparatus of the invention is generally denoted as a schematic block diagram by the numeral 10. The apparatus (10) includes generally a vacuum pump (11), a fluidic gate (12), a calibration gas input system (13), a span calibration gas system (14), and a zero calibration gas system (16).

A monitored oven system may be seen as depicted by the numeral 17. A pickup tube (18) placed in pneumatic communication with the oven system (17) atmosphere provides a fluid pathway from the monitored environment to the analyzer (19).

The analyzer (19) may be of any suitable type capable of analyzing and determining the concentration level of one or more selected gases. The analyzer (19) includes an input port (21) for receiving gases from the apparatus (10). Gases are drawn through the pickup tube (18) and through the analyzer (19) by vacuum, and after being analyzed, are withdrawn through an analyzer exhaust port (22). Eventually, such analyzed and exhausted gases may be returned to the oven system (17) by an exhaust tube (23) as depicted. The apparatus (10) described herein operably connects between the oven system (17) and the analyzer (19).

The vacuum pump (11) of the apparatus (10) has a vacuum input port (24) and a compression output port (26). The vacuum input port (24) operably connects to the analyzer exhaust port (22) by means of an appropriate pneumatic pathway (27). The compression output port (26) operably connects to the exhaust tube (23) located in the oven system (17) by means of a similar pneumatic pathway (28).

Figure 2:
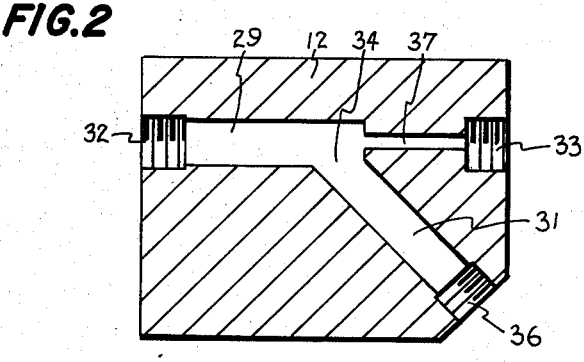
FIG. 2 is an enlarged cross-sectioned front elevational view of the fluidic gate of the invention.

Referring to FIG. 2, the fluidic gas (12) of the apparatus (10) may be formed of a block of some suitable metal such as steel. Although materials other than metal might be operable, the fluidic gate (12) should be heated to prevent condensation of the test gases, and steel works well for this purpose. The fluidic gate (12) may be so heated by any appropriate method (30).

The fluidic gate (12) includes first and second pathways (29 and 31) disposed therethrough. The first pathway (29) defines a passage completely through the block, forming a test gas input (32) at one end and a calibration gas input (33) at the end opposite. The second pathway (31) intersects the first pathway (29), forming a pneumatic juncture (34) at the intersection and an output port (36) at the opposing end. To facilitate connecting the fluidic gate (12) to the various components of the apparatus (10), the test gas input (32), the calibration gas input (33) and the output port (36) may all be tapped as shown to receive a threaded pipe member or the like.

Preferably, a venturi (35) (FIG. 5) or other restricted conduit (37) (FIG. 2) may be formed in the first pathway (29). This venturi (35) or other restricted conduit (37) should be located between the calibration gas input (33) and the pneumatic juncture (34) of the first and second pathway. Ideally, the venturi (35) or other restricted conduit (37) will terminate just short of the juncture (34) for reasons to be made more clear below.

Referring again to FIG. 1, a first flow adjustment needle valve (38) connects to the calibration gas input (33) and a second flow adjustment needle valve (39) connects to the output port (36) of the fluidic gate (12). These valves (38 and 39) regulate the proper flow of calibration gases through the calibration gas input (33) and the proper flow of gases through the output port (36) and into the analyzer (19). Such flow adjustment needle valves (38 and 39) may be manually or electrically operable, and may be made sensitive to various operating parameters of the system, if desired. The applicants have determined that needle valves such as the Norgren 17-001-006 work well in the above application.

The calibration gas input system (13) includes two solenoid valves (41 and 42), a pressure regulator (43) and appropriate lengths of sealed tubing as shown. The first solenoid valve (41) has one output port (44) and two input ports (46 and 47) such as a Skinner V54 Type solenoid valve. This solenoid valve (41) selectively connects the output port (44) to one or the other of the inputs (46 and 47). The output port (44) of the input-selective solenoid valve (41) connects to the input port (48) of a pressure regulator (43), such as a Fisher Controls Type 912. This pressure regulator (43) serves to maintain the calibration gases at a suitable pressure level.

The output port (49) of the pressure regulator (43) operably connects to the input port (51) of a calibration gas line solenoid valve (42) such as a Skinner V52 Type. This valve (42) has its output port (52) connected through the first flow adjustment needle valve (38) described above to the calibration gas input (33) of the fluidic gate (12). This solenoid (42) may be electrically operated, and operates to selectively close or open the pneumatic passageway into the gas calibration input (33) of the fluidic gate (12). Although such a solenoid valve may not operate reliably when placed in a test gas conduit for reasons made apparent above, it will operate satisfactorily in a calibration gas conduit, since calibration gases do not contain the resins and solvents that tend to clause clogging.

The span calibration gas system (14) includes an appropriate input port (53) connected by tubing (54) to an input port (46) of the input-selective solenoid valve (41) of the calibration gas input system (13) described above. This input port (46) should be suitable for receiving the contents of containers of pressurized span calibration gas (not shown).

The zero calibration gas system (16) includes in part a vacuum breaker (56) having an input port (57) open to atmospheric gases and an output port (58) connected to the vacuum input port (24) of the vacuum pump (11). By these connections, atmospheric gases may be introduced by way of the vacuum pump (11) through the vacuum breaker (56), and these atmospheric gases can be used as a zero calibration gas. A Cash FRM-VO may be used as such a vacuum breaker (56).

To facilitate the introduction of atmospheric gases into the calibration gas input system (13) the compression output port (26) of the vacuum pump (11) connects through suitable pneumatic conduit (54) to the remaining input (47) of the input-selective solenoid valve (41) of the calibration gas input system (13). Atmospheric gases may be drawn by the vacuum pump (11) through the vacuum breaker (56) and then forced out the compression output port (26) of the vacuum pump (11) and through this solenoid valve (41) into the calibration gas input (33) of the fluidic gate (12).

It has been determined that the flow of atmospheric gases into the input-selective solenoid valve (41) may be enhanced by placing a restriction valve (61) in the compression output conduit (28) subsequent to the interaction of the conduit (59) connecting the input-selective solenoid valve (41) with the compression output port (26) of the vacuum pump (11). Suitably adjusted, the pressure in the compression output conduit (28) will be higher on the vacuum pump side of the restriction valve (61) than on the oven system side.

To prevent undesirable condensation of the test gases, the conduit (62) linking the output port (36) of the fluidic gate (12) with the input port (21) of the analyzer (19) may be heated by any appropriate means.

Figure 3:
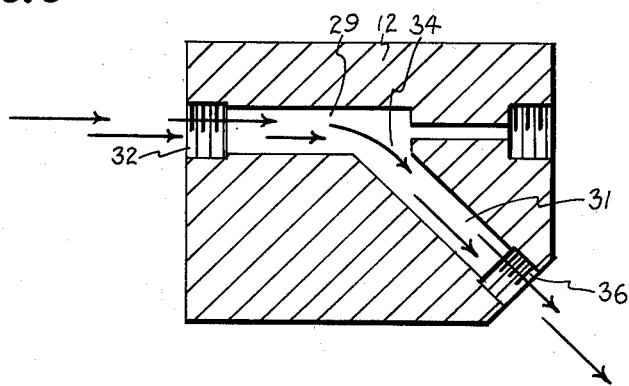
FIG. 3 is the fluidic gate as depicted in FIG. 2 and further illustrating the flow of test gases through the gate.

It may now be seen that the apparatus (10) provides for a normal monitoring mode of operation and two calibration modes of operation. In the normal monitoring mode, the calibration gas line solenoid valve (42) will be closed, and the vacuum pump (11) will suck gases from within the oven system (17) and through the fluidic gate (12) as depicted in FIG. 3. Since the pathway for test gases through the fluidic gate (12) contains no sharp turns, undesirable buildups of solvents, resins and the like will not be so likely to accummulate. Referring back to FIG. 1, the test gases will be passed through the analyzer (19) where appropriate sensors will determine the concentration level of the monitored gases. The gases will then be drawn out of the analyzer (19) through the vacuum pump (11) and pumped back into the monitored environment.

Figure 4:
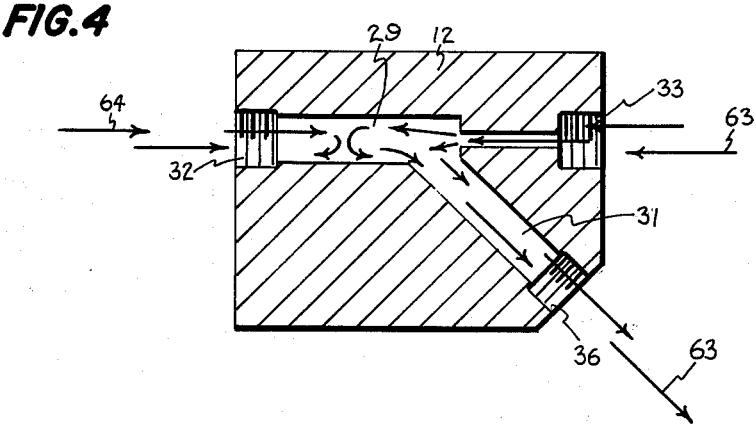
FIG. 4 is the fluidic gate as depicted in FIG. 2 and further illustrating the flow of test gases being blocked by the flow of calibration gases, and further illustrating the flow of calibration gases through the output port thereof.

In the span calibration gas mode, the calibration gas line solenoid valve (42) opens the calibration gas line. The input-selective solenoid valve (41) will then be adjusted to allow the pressurized span calibration gas to flow therethrough and enter the calibration gas input (33) of the fluidic gate (12) as depicted in FIG. 4. The span calibration gas (63) will be forced through the venturi (35) or other restricted conduit (37) in the fluidic gate (12) and will exit therefrom at significant pressure. This pressure will completely block the flow of test gases (64) such that no test gases (64) may be introduced into the analyzer (19). Partly because of the accute angle between the calibration gas input (33) and the second pathway (31) of the fluidic gate (12), however, the span calibration gas (63) will not enter the second pathway (31) under pressure. In fact, since the mouth (34) of the second pathway (31) intersects the first pathway (29) just forward of the venturi (35) opening, a low pressure area will exist at the mouth (34) such that the analyzer (19) may continue to receive gases at a demand rate regulated by the suction of the vacuum pump (11). The fluidic gate (12) therefore operates to block the flow of test gases (64) to the analyzer (19) while simultaneously supplying calibration gases to the analyzer (19) at the analyzer's own demand rate. Since the calibration gases are not delivered to the analyzer (19) under pressure, the integrity of the calibration process is further insured.

In the remaining calibration mode, the input-selective solenoid valve (41) is adjusted to connect the second input (47) with the output (44) such that atmospheric gases may flow into the calibration gas input (33) of the fluidic gate (12) as described above. The flow of these atmospheric gases will block the flow of test gases and will be available for transport to the analyzer (19) upon vacuum demand in the same manner as described above.

Upon completing calibration, the apparatus (10) may be returned to the normal monitoring mode by closing the calibration gas line solenoid valve (42) thereby stopping the flow of gases through the calibration gas input (33) of the fluidic gate (12). Test gases will then again flow through the fluidic gate (12) and into the analyzer (19).

If desired, the apparatus (10) could provide for automatic calibration by making the above valves operate automatically in timed sequence. Furthermore, many other changes to the disclosed embodiment will be readily apparent to those skilled in the art. Therefore, while we have described the best mode known for carrying out the invention, it will be understood that various changes, adaptations, and modifications may be made therein without departing from the spirit of the invention and the scope of the appended claims.

What is claimed is:

1. In a gas analyzer calibration apparatus suitable for use with a gas analyzer, an improvement comprising a fluidic gate for selectively routing a test gas or a calibration gas to the analyzer, said fluidic gate including:
   (a) first input means for receiving a test gas at a preselected rate of flow;
   (b) second input means for receiving a calibration gas at a second preselected rate of flow that exceeds the first preselected rate of flow;
   (c) output means for exiting gases from said fluidic gate to an analyzer;
   (d) gate means for substantially blocking a flow of a test gas through said output means in response to a flow of a calibration gas through said second input means and for allowing such calibration gas to exit said fluidic gate through said output means at a rate of flow substantially equal to the first preselected rate of flow, without substantially altering pressure within said output means upon receiving a calibration gas within said second input means.

2. The fluidic gate of claim 1 wherein said fluidic gate may be heated to prevent the condensation or partial condensation of a test gas flowing therethrough.

3. A fluidic gate suitable for use in gas analyzer calibration apparatus comprising:
   (a) a first substantially straight and enclosed pneumatic pathway having a first end and a second end;
   (b) a second substantially straight and enclosed pneumatic pathway having a first end that pneumatically intersects said first pneumatic pathway and a second end, said second pathway being disposed to form an acute angle between said second pathway and the second end of said first pathway.

4. The fluidic gate of claim 3 wherein at least part of said fluidic gate may be heated such that a test gas flowing through said first and second pathway will not condense.

5. In a gas analyzer calibration apparatus suitable for use with a gas analyzer, an improvement comprising:
   (a) fluidic gate means for selectively allowing test gases or calibration gases to enter a gas analyzer;
   (b) vacuum pump means for providing a vacuum line input and a compression line output;
   (c) vacuum breaker means having an input open to atmospheric gases and being operably connected to said vacuum line input for introducing atmospheric gases into the vacuum pump means;
   (d) valve means for selectively connecting the output of said vacuum pump means to an input of said fluidic gate means, such that atmospheric gases may be selectively allowed to enter said analyzer through said fluidic gate.

6. The fluidic gate of claim 3 and further including a restricted conduit formed in said first pathway between the intersection of said first and second pathway and the second end of said first pathway.

* * * * *